United States Patent
Contino-Pepin et al.

(10) Patent No.: US 12,016,957 B2
(45) Date of Patent: Jun. 25, 2024

(54) PROCESS FOR EXTRACTING SUBSTANCES OF INTEREST

(71) Applicants: AVIGNON UNIVERSITE, Avignon (FR); LYOFAL, Salon-de-Provence (FR); Centre National de la Recherche Scientifique, Paris (FR); ECOLE NATIONALE SUPERIEURE DE CHIMIE DE MONTPELLIER, Montpellier (FR); UNIVERSITE DE MONTPELLIER, Montpellier (FR)

(72) Inventors: Christiane Contino-Pepin, Althen des Paluds (FR); Stéphane Desgranges, Avignon (FR); Alice Dall'armellina, Avignon (FR); Charles Duval, Eyguieres (FR); Mathias Letan-Martin, Robion (FR)

(73) Assignees: AVIGNON UNIVERSITE, Avignon (FR); LYOFAL, Salon-de-Provence (FR); CENTRE NATIONAL DE LA RECHERCHE SCIENTIFIQUE, Paris (FR); ECOLE NATIONALE SUPERIEURE DE CHIMIE DE MONTPELLIER, Montpellier (FR); UNIVERSITE DE MONTPELLIER, Montpellier (FR)

( * ) Notice: Subject to any disclaimer, the term of this patent is extended or adjusted under 35 U.S.C. 154(b) by 334 days.

(21) Appl. No.: 17/297,530

(22) PCT Filed: Nov. 27, 2019

(86) PCT No.: PCT/EP2019/082797
§ 371 (c)(1),
(2) Date: May 27, 2021

(87) PCT Pub. No.: WO2020/109418
PCT Pub. Date: Jun. 4, 2020

(65) Prior Publication Data
US 2022/0008340 A1 Jan. 13, 2022

(30) Foreign Application Priority Data

Nov. 27, 2018 (FR) ........................... 1871961
Mar. 19, 2019 (FR) ........................... 1902826

(51) Int. Cl.
| | | |
|---|---|---|
| A61K 36/00 | (2006.01) | |
| A23L 33/105 | (2016.01) | |
| A61K 9/19 | (2006.01) | |
| A61K 36/53 | (2006.01) | |
| A61K 36/752 | (2006.01) | |
| A61K 36/9066 | (2006.01) | |
| A61K 47/14 | (2017.01) | |
| A61K 47/44 | (2017.01) | |
| B01D 11/02 | (2006.01) | |

(52) U.S. Cl.
CPC .............. *A61K 9/19* (2013.01); *A23L 33/105* (2016.08); *A61K 36/53* (2013.01); *A61K 36/752* (2013.01); *A61K 36/9066* (2013.01); *A61K 47/14* (2013.01); *A61K 47/44* (2013.01); *B01D 11/0265* (2013.01); *A23V 2002/00* (2013.01); *A61K 2236/331* (2013.01); *A61K 2236/35* (2013.01); *A61K 2236/51* (2013.01)

(58) Field of Classification Search
CPC .................................. A61K 8/062; A61K 9/19
See application file for complete search history.

(56) References Cited

FOREIGN PATENT DOCUMENTS

| CN | 101978996 B | | 1/2012 |
|---|---|---|---|
| CN | 103301076 A | * | 9/2013 |
| FR | 2903016 A1 | | 1/2008 |
| KR | 2014-0115427 A | | 10/2014 |
| KR | 2015-0107504 A | | 9/2015 |

OTHER PUBLICATIONS

Sui et al, Impact of ultrasonic treatment on an emulsion system stabilized with soybean protein isolate and lecithin: Its emulsifying property and emulsion stability. Food hydrocolloids (2017), vol. 63, pp. 727-734 (Year: 2017).*

Gallegos et al, Droplet-size distribution and stability of lipid injectable emulsions. Pharmacists, (Jan. 15, 2009) vol. 66, No. 2, pp. 162-166 (Year: 2009).*

(Continued)

*Primary Examiner* — Qiuwen Mi
(74) *Attorney, Agent, or Firm* — Osha Bergman Watanabe & Burton LLP

(57) ABSTRACT

The present description relates to a method for extracting at least one substance of interest, the method comprising the following steps: —providing an admixture comprising water, a source comprising the at least one substance of interest or at least one precursor thereof, at least one surfactant and at least one lipophilic compound; —the emulsification of the admixture, leading to the formation of an emulsion; wherein the emulsion comprises: —a continuous aqueous phase; and a discontinuous lipidic phase comprising the at least one lipophilic compound, the at least one surfactant and at least one substance of interest extracted from the source during the emulsification; wherein the method further comprises the addition of at least one cryoprotectant to the admixture and the lyophilization of the emulsion.

10 Claims, 1 Drawing Sheet

(56) References Cited

OTHER PUBLICATIONS

International Search Report issued in Application No. PCT/EP2019/082797, mailed on Feb. 24, 2020 (8 pages).
Written Opinion issued in International Application No. PCT/EP2019/082797, mailed on Feb. 24, 2020 (9 pages).
Nguyen, H T P et al.; "Novel alginate-based nanocarriers as a strategy to include high concentrations of hydrophobic compounds in hydrogels for topical application;" Nanotechnology, Institute of Physics Publishing; vol. 26; No. 25; Jun. 2, 2015 (13 pages).
Dima et al.; "Encapsulation of Functional Lipophilic Food and Drug Biocomponents;" Food Engineering Reviews, Springer; vol. 7; No. 4; Mar. 4, 2015; pp. 417-438 (22 pages).

* cited by examiner

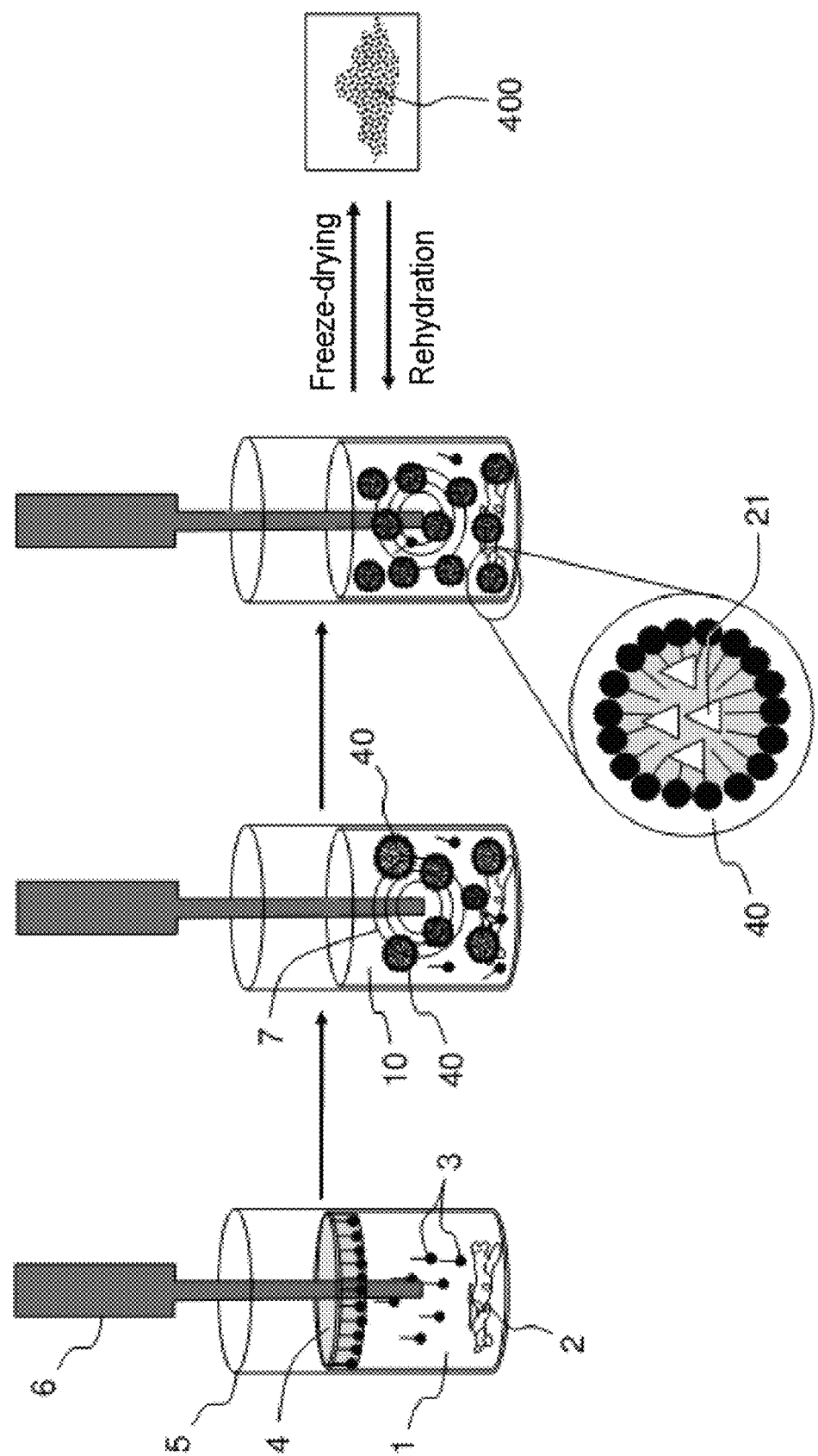

PROCESS FOR EXTRACTING SUBSTANCES OF INTEREST

TECHNICAL FIELD OF THE INVENTION

The present description relates to a process for extracting at least one substance of interest, to emulsions produced by such a process, and to uses of such emulsions. The present description has applications in particular, but not exclusively, in the fields of food processing, cosmetics and pharmaceuticals, and in the field of perfumes.

STATE OF THE ART

Natural substances, such as for example those of plant, animal or mineral origin, are of growing interest in a number of fields. Indeed, given the great molecular chemodiversity offered by the plant kingdom, for example, and the general public's craze for natural products, a certain number of industrial sectors (cosmetics, pharmaceuticals, food processing, nutraceuticals, probiotics) are turning to the incorporation of molecules of plant origin in their formulations. Adding value to these natural active principles represents a significant economic potential for the breeding ground of companies in the food processing, cosmetic and pharmaceutical sectors.

For value to be added, natural compounds such as bioactive compounds, i.e., compounds having biological activity, can first be separated from their plant matrix during an extraction step, before being used as such, in extract form, or after purification in the form of isolated molecules. The extraction sector is particularly concerned by environmental and economic issues and is today trying to find solutions in order to reduce energy costs and waste throughout the extraction process chain.

In the field of extraction of natural products with high added value, solvent extraction remains the most commonly used method. However, this extraction relies on organic solvents such as hexane, cyclohexane, petroleum ether, methanol, ethanol or the use of hydroalcoholic mixtures. For example, if the natural product to be extracted, i.e., the substance of interest, is hydrophilic, the extraction solvent used may be polar aprotic such as acetone, or polar protic such as water, methanol or ethanol. If, on the other hand, the natural product to be extracted, i.e., the substance of interest, is lipophilic, the extraction solvent used can then be apolar, i.e., hydrophobic, such as hexane, or less apolar than hexane, such as chloroform or dichloromethane. A great many of these solvents are flammable, volatile and toxic. Furthermore, the gradual depletion of oil resources, and especially the tightening of regulations, are forcing manufacturers to move towards more environmentally friendly processes. The search for alternatives to the use of organic solvents and/or energy-consuming extraction processes, sometimes denaturing the biomolecules, is both a major economic and scientific challenge to which the present invention responds.

Despite the ubiquitous nature of water in plants, many bioactive molecules of plant origin (such as vitamins, antioxidants, natural anti-inflammatories, etc.) are poorly soluble or insoluble in water, which limits the extraction yields and the quality (for example in terms of integrity and stability) of the extracts produced.

The subject matter of the present description is, inter alia, a process which, in certain embodiments, can make it possible to extract, without altering them and with good yields, substances of interest, for example liposoluble substances, of plant, animal or mineral origin by emulsification, e.g., by sonication, of an aqueous medium to which a lipophilic compound and a synthetic or natural surfactant have been added, and to obtain in the same step ("one-pot"), a formulation that is stable over time and easy to store and transport.

SUMMARY OF THE INVENTION

In the present description and in the following claims, the term "comprise" is synonymous with (means the same as) "include," "contain," and is inclusive or open-ended and does not exclude other elements not described or represented. Further, in the present description, the term "about" is synonymous with (means the same as) a lower and/or upper margin of 10%, for example 5%, of the respective value.

In the present description and in the claims, D means the mean droplet diameter, measured with a granulometer, based on light diffraction, for droplets of diameter D greater than 1000 nm (De Brouckère volume-weight mean diameter of the emulsion particles), and with a dynamic light scattering (DLS) apparatus for droplets of diameter D less than 1000 nm. When the dynamic light scattering (DLS) apparatus is used to measure D, the polydispersity index (PdI) of an emulsion is defined as the ratio of the square of the standard deviation to the square of the mean droplet diameter. When the granulometer is used, polydispersity index (PdI) of an emulsion means the ratio D90/D10, where droplet diameter D10 means the droplet diameter for which 90% of the total population of droplets in the emulsion have a diameter greater than or equal to this value, and D90 means the droplet diameter for which 10% of the total population of droplets in the emulsion have a diameter greater than this value.

One objective of the present description is to provide a process for extracting at least one substance of interest from a source. The at least one substance of interest may either be contained in the source, or be generated by said extraction process in the case where the at least one substance of interest is derived from at least one molecule previously contained in said source, which, during the extraction process, is chemically transformed into said at least one substance of interest.

According to a first aspect, the present description relates to a process for extracting at least one substance of interest from a source, the process comprising the following steps of:
  providing a mixture comprising water, a source comprising the at least one substance of interest or at least one precursor thereof, at least one surfactant, and at least one lipophilic compound;
  emulsifying said mixture, thereby forming an emulsion;
  and wherein said emulsion comprises:
    a continuous aqueous phase; and
    a discontinuous lipid phase comprising the at least one lipophilic compound, said at least one surfactant, and the at least one substance of interest extracted from said source during emulsifying;
  wherein the source is a plant, an animal, a mineral, a prokaryote, and/or a unicellular eukaryote source;
  wherein the process further comprises adding at least one cryoprotectant to the mixture and freeze-drying the emulsion and wherein adding at least one cryoprotectant to the mixture is performed after emulsifying the mixture, in a weight-to-volume ratio of at least 5% w/v based on the total volume of the mixture excluding the source.

The process according to the embodiments of the present description can advantageously be "one-pot", without altering the at least one substance of interest and with good yields of substance of interest. The extraction of molecules by emulsification, in an aqueous medium to which lipophilic compound and surfactant has been added, meets a "green chemistry" and environmentally-friendly approach.

According to one or more embodiments, emulsifying the mixture comprises applying an energy source to the mixture, which may be ultrasonic energy and/or purely mechanical energy. According to one or more embodiments, emulsifying the mixture comprises sonicating the mixture. Sonicating the mixture comprises applying an ultrasonic energy source to the mixture, leading to the formation of an emulsion. Thus, the process comprises emulsifying a mixture comprising water, a source comprising the at least one substance of interest or at least one precursor thereof, at least one surfactant, and at least one lipophilic compound. Emulsifying this mixture leads to the formation of an emulsion comprising a continuous aqueous phase and a discontinuous lipid phase comprising the at least one lipophilic compound, said at least one surfactant and at least one substance of interest extracted from said source, during emulsifying. Emulsifying induces the formation of an emulsion, which has the effect of increasing the contact surface between the two aqueous and lipid phases, and thus the transfer of the at least one substance of interest from one phase to the other. According to one or more embodiments, after emulsifying the mixture leading to the formation of the emulsion, a residual portion of the surfactant may be included in the aqueous phase.

According to one aspect, the present description relates to a process for extracting at least one substance of interest from a source, the process comprising the following steps of:
  providing a mixture comprising water, a source comprising the at least one substance of interest or at least one precursor thereof, at least one surfactant, and at least one lipophilic compound;
  sonicating said mixture, thereby forming an emulsion; and wherein said emulsion comprises:
    a continuous aqueous phase; and
    a discontinuous lipid phase comprising the at least one lipophilic compound, the at least one surfactant and the at least one substance of interest extracted from said source during sonicating;
wherein the source is a plant, an animal, a mineral, a prokaryote, and/or a unicellular eukaryote source;
wherein the process further comprises adding at least one cryoprotectant to the mixture and freeze-drying the emulsion and wherein adding at least one cryoprotectant to the mixture is performed after emulsifying the mixture, in a weight-to-volume ratio of at least 5% w/v based on the total volume of the mixture excluding the source.

By taking advantage of the lipophilic nature of certain molecules that are difficult to extract in pure water (e.g., without adding alcohol), the inventors were able to achieve an extraction process in water to which at least one lipophilic compound and surfactants of natural or synthetic origin have been added, making it possible to obtain, in a limited number of steps, extracts of the "oil and/or wax in water" type, enriched in potentially bioactive molecules of interest.

According to one or more embodiments, the source may be, for example, a plant (such as olive pomace, lees, winemaking residues, etc.), an animal (such as carcasses, skins, or other parts of animals), a mineral, a prokaryote, and/or a unicellular eukaryote source.

The source may be derived from by-products of the food and/or agricultural industry, whether plant, animal, mineral, prokaryote, and/or unicellular eukaryote or other.

The source may consist of any material that may contain or give rise to at least one substance of interest. A substance of interest may, for example, comprise a lipophilic molecule that is poorly soluble in water (liposoluble) and is of potential interest for an application in the cosmetic, pharmaceutical and/or food processing field. Said molecule may for example have a biological activity with a beneficial effect on human health. Antioxidants, for example, are molecules which can play a predominant role in protecting the body against the development of cardiovascular diseases and certain cancers, in particular due to their ability to rapidly trap the reactive oxygen species involved in the development of these diseases. Said lipophilic molecule may for example comprise a polyphenol or a terpene.

According to one or more embodiments, the source is a plant source. The plant source may contain at least a portion of at least one plant (seed, leaf, root, stem, fruit, flower, etc.). The plant source may be cited, for example, in the book by Albert Y. Leung and Steven Foster, "Encyclopedia of common natural ingredients used in food, drugs and cosmetics", $2^{nd}$ edition, Wiley-Interscience, 1996. The plant source may for example be selected from plant sources associated with soothing properties, anti-inflammatory properties, antiseptic properties, antiperspirant properties, calming properties, healing properties, tonic properties, properties promoting the containment of blood and lymphatic microcirculation, texturizing properties, antioxidant properties, foaming or emulsifying properties, photoprotective properties, thickening, absorbing and/or odorant properties.

By way of examples of plant sources classified according to their different properties, particular mention may be made of:
  for their soothing properties: apricot, blueberry, white broth, Roman chamomile, *Matricaria*, poppy, fenugreek, marshmallow, flax, lily, mallow, marigold, elderberry, linden, coltsfoot, *psyllium*, plantain, quince, peach, orange, cactus, apple; for their anti-inflammatory properties: agrimony, hawthorn, heather, couch grass, juniper, marshmallow, elder, linden, fenugreek, gentian, lettuce, wild pansy, plantain, bramble, rosemary, sage, black bryony, coltsfoot, immortelle, daisy;
  for their antiseptic properties: garlic, agrimony, bilberry, burdock, oak, comfrey, *eucalyptus*, juniper, rose geranium, laurel, lavender, marjoram, mint, pine, rosemary, sandalwood, thyme, sage, honeysuckle, immortelle, daisy, tansy, chili pepper, pepper;
  for their antiperspirant properties: sage, oak, walnut, pine, horsetail, coltsfoot;
  for their astringent properties: acacia, yarrow, agrimony, lady's mantle, arbutus, mugwort, comfrey, cypress, oak, rosehip, witch hazel, black mulberry, blueberry, hazelnut, walnut, nettle, poplar, plantain, bramble, ratanhia, rose, loosestrife, willow, tormentil, red vine, sweet clover;
  for their calming properties: carrot, wild pansy, elderberry, linden, passionflower, basil, camphor, pear, apple, vine, lettuce, rose, ginger;
  for their healing properties: St. John's wort, silverweed, marigold, *Matricaria*, Roman chamomile, comfrey, yarrow, wormwood, agrimony, mugwort, *arnica*, chervil, myrtle, periwinkle, plantain, poplar, primrose, sage, ragwort, elderberry, *verbena, angelica*, birthwort, alder, aurone, bistort, birch, blessed thistle, juniper, medlar, *eucalyptus*, kidney vetch, bennet, centaury, cabbage, houseleek, strawberry, horsetail, meadowsweet, coltsfoot, wild pansy, burdock, daisy, lily;

for their tonic properties: St. John's wort, rosehip, mistletoe, mate, blackcurrant, wormwood, *arnica*, calamint, cinnamon, geranium, hyssop, marjoram, lemon balm, parsley, Scots pine, rosemary, savory, wild thyme, basil, rose hip, gentian, hop, white bay, mint, sage, tormentil, yarrow, agrimony, bennet, bistort, oak, quince, cypress, horse chestnut, medlar, walnut, nettle, plantain, water pear, cinquefoil, knotweed, loosestrife, speedwell, *angelica*, mugwort, woodruff, juniper, mustard, cinchona, fumitory, nasturtium, watercress, kelp, butcher's broom, tansy;

for their properties promoting the contention of the blood and lymphatic microcirculation: blackcurrant, bilberry and grape seeds;

for their texturizing properties: wheat, rockweed;

for their antioxidant properties: rice, rosemary, sage, thyme, green tea, licorice, pepper;

for their foaming or emulsifying properties: *saponaria*, ivy, butcher's broom, panama wood, Quillaja, sarsaparilla, *quinoa*, soy;

for their photoprotective properties: aloe, sunflower, licorice, *magnolia*, Kaempferia;

for their thickening or absorbing properties: pea, wheat, potato, corn; and for their fragrant properties: rosemary, violet, lavender, jasmine, lily of the valley, vanilla, rose, citrus fruits, e.g., lemon, grapefruit. According to one or more embodiments, the plant source is the *Curcuma longa* plant.

According to one or more embodiments, the source comprises propolis and/or honey. The at least one lipophilic compound may be contained in the source and/or result from a prior exogenous addition. Depending on the source considered, the exogenous addition of the at least one lipophilic compound will not always be necessary to obtain a stable emulsion. For example, certain plant matrices can release essential oils, phospholipids and amphiphilic proteins under the effect of ultrasound. For example, citrus peels can release a variable amount of essential oil under the effect of ultrasound, which may be sufficient to obtain the emulsions targeted by the process according to embodiments of the present description. According to one or more embodiments, the at least one lipophilic compound is selected from the group consisting of oils, waxes, and combinations thereof. The at least one lipophilic compound may, for example, comprise a mixture between multiple oils, between multiple waxes, or an oil(s)/wax(es) mixture. The inventors have found that for some sources, the presence of at least two lipophilic compounds in the mixture provided by the process of the invention can reduce the polydispersity index of the emulsion and/or decrease the mean diameter D of the droplets of the emulsion and/or increase the extraction rate of the at least one active substance, e.g., in the presence of two different oils, or an oil and a wax, as opposed to the case where only one oil is present in the mixture. According to one or more embodiments, the lipophilic compound is selected from the group consisting of mono-, di- or triesters of glycerol, or derivatives of glycerol, mono-, di- or tri- or tetraesters of citric acid or derivatives of citric acid, fatty acids, monoesters of fatty acids, essential oils, fat substitutes, waxes, and combinations thereof. Advantageously, the process according to the present description does not require the use of a typical organic extraction solvent, such as for example hexane, cyclohexane, dichloromethane, tetrahydrofuran, dimethyl sulfoxide, petroleum ether, methanol, ethanol, or a hydroalcoholic mixture.

According to one or more embodiments, the at least one lipophilic compound is present in the mixture, excluding the source, in a weight-to-volume ratio comprised between 0.01% w/v and 70% w/v, for example between 3% w/v and 70% w/v, based on the total volume of the mixture comprising water, lipophilic compound and surfactant. The weight-to-volume ratio of the at least one lipophilic compound in the same mixture, excluding the source, is for example comprised between 0.1% w/v and 20% w/v, for example between 5% w/v and 20% w/v.

The at least one surfactant may be anionic, cationic, zwitterionic, amphoteric or nonionic. The at least one surfactant may be natural or synthetic. According to one or more embodiments, its hydrophilic-lipophilic balance (HLB) is comprised between 4 and 19. The at least one surfactant may, for example, be selected from the group comprising nonionic surfactants such as alcohols, amino alcohols, esters, amine oxides, and combinations thereof. The surfactant may be, for example, Lauroglycol™ FCC (Propylene glycol monolaurate (type I)), Lauroglycol™ 90, Capryol™ 90, Plurol® Oleique CC 497 (Polyglyceryl-3 dioleate), Labrasol®, Caprylocaproyl Polyoxyl-8 glycerides, Labrafil® M 1944 CS, Labrasol® ALF, Labrafil® M 2125 CS, Gelucire® 50/13, Labrafil® M 2130 CS, Gelucire® 48/16, Gelucire® 44/14, Transcutol® HP, Emulfree® CBG MB. The surfactant can be selected from the group consisting of Axol C62 (ADARA), Cutina CP (BASF), Cutina GMS (BASF), Emulium 22 (GATTEFOSSE), Emulium Delta (GATTEFOSSE), Emulium melifera (GATTEFOSSE), Eumulgin SG (BASF), Montanov 202 (Seppic), Montanov 68 (Seppic), Montanov 82 (Seppic), Montanov L (Seppic), Olivem 1000 (Univar), Olivoil avenate (ACS Phyto), Xyliance (MASSO).

The surfactant can be derived from sugars, such as an alkyl polyglycoside, a sorbitan ester, a sucrose ester (or sucroester), or an alkylmethylglucamide. For example, the surfactant may be an alkyl polyglycoside, such as an alkyl polyglucoside. Alkyl polyglycosides are a class of nonionic surfactants widely used in various cosmetic, household and industrial applications. Biodegradable, these surfactants are generally derived from glucose and fatty alcohols. The sugar-derived surfactant can also be a fatty acid sucroester, or sucrose ester of fatty acid, such as for example E473. Fatty acid sucroesters are listed in the Codex Alimentarius as emulsifiers and stabilizers. Among other uses, sucroesters are added to ice cream, confectionery, chewing gums, spirits, food supplements, infant and young child formulas, as well as in the surface treatment of fresh fruit. Apart from processed food, sucroesters can be used in cosmetic and pharmaceutical products, e.g., as emulsifiers for creams, cleansing lotions, lotions and ointments. The sugar surfactant can also be a sorbitan ester, such as E491 (Sorbitan monostearate, Span 60), E492 (Sorbitan tristearate, Span 65), E493 (Sorbitan monolaurate, Span 20), E494 (Sorbitan monooleate, Span 80), E495 (Sorbitan monopalmitate, Span 40), E496 (Sorbitan trioleate, Span 85), E432 (Polyoxyethylene sorbitan monolaurate, Polysorbate 20), E433 (Polyoxyethylene sorbitan monooleate, Polysorbate 80), E434 (Polyoxyethylene sorbitan monopalmitate, Polysorbate 40), E435 (Polyoxyethylene sorbitan monostearate, Polysorbate 60), E436 (Polyoxyethylene sorbitan tristearate, Polysorbate 65). The sugar-derived surfactant may be selected from the group consisting of Simulsol AS 48, Simulsol SL 7G, Coco Glucoside, Decyl Glucoside, Lauryl Glucoside, Sodium Lauryl Glucose Carboxylate.

The surfactant can also be derived from amino acids, such as Sodium Cocoyl Glutamate, Disodium Cocoyl Glutamate, Sodium Lauroyl Glutamate, derived from peptides, such as Sodium Cocoyl Hydrolyzed Wheat Protein, Sodium Cocoyl Hydrolyzed Collagen. The surfactant can be an alkyl PEG sulfosuccinate such as Disodium Laureth Sulfosuccinate, Disodium Deceth Sulfosuccinate, an acylsarcosine such as Sodium Lauroyl Sarcosinate, Sodium Cocoyl Sarcosinate, an acyl isethionate such as Sodium Cocoyl Isethionate. The surfactant can be Disodium Laureth Sulfosuccinate, Cocamidopropyl Betaine, Coco Betaine, Sodium Coco Sulfate, Sodium Lauryl Sulfoacetate. The surfactant can be a glycolipid such as rhamnolipids (RL), mannosylerythritol lipids (MEL), trehalipids (TL), xylolipids, sophorolipids, a lipopeptide such as fengycin, iturin, surfactin.

According to one or more embodiments, the at least one surfactant is selected from the group comprising dendrimers, such as, for example, those of the Dendri-TAC type described in application PCT/IB2016/052952, oligomers of the $F_iTAC_n$ or $H_iTAC_n$ type, TPGS 1000, TPGS 750M, and combinations thereof. For each surfactant, the surfactant concentration can for example be adapted to the lipophilic compound concentration in order to obtain emulsions with a low polydispersity index, and thus influence the extraction yield and/or the purity of the substance of interest. According to one or more embodiments, the surfactant concentration in the mixture excluding the source is comprised between 0.5 mg/mL and 250 mg/mL, for example between 5 mg/mL and 250 mg/mL. Above the upper limit of this range, the extraction yield of substance(s) of interest may decrease. This decrease may result from increased viscosity leading to difficulties in transferring the substance(s) of interest from the source to the discontinuous lipid phase of the emulsion.

According to one or more embodiments, emulsifying is performed by maintaining the temperature of the mixture between about 0° C. and about 60° C., for example between 4° C. and 60° C.

According to one or more embodiments, the temperature of the emulsion or formulation does not exceed 60° C. during the process. In particular for substances of interest that are susceptible to rapid degradation in the presence of air and/or when undergoing heat treatment, the process according to these embodiments thus provides considerable added value in the cosmetic, food and/or pharmaceutical sectors.

According to one or more embodiments, the temperature of the mixture does not exceed 25° C. during emulsifying, and remains for example comprised between 0° C. and 20° C., for example between 5° C. and 15° C.

According to one or more embodiments, emulsifying can be performed by means of an ultrasonic bath and/or an ultrasonic rod (sonotrode) and/or an ultrasonic cup-horn type reactor and/or a disperser-homogenizer (for example Ultraturrax® type).

According to one or more embodiments, the mixture is stirred during emulsifying.

According to one or more embodiments, the duration of emulsifying is between about 0.5 seconds and about 5 hours. According to one or more embodiments, the duration of emulsifying does not exceed 2 hours, and is for example comprised between 0.5 hours and 1.5 hours.

According to one or more embodiments of the process wherein emulsifying the mixture comprises sonicating the mixture, sonicating is performed at a power comprised between about 100 W and about 800 W, at a frequency comprised between about 20 kHz and about 2000 kHz, in pulsed or continuous mode.

According to one or more embodiments, the discontinuous lipid phase is in the form of droplets of a predetermined mean diameter (D). According to one or more embodiments, the predetermined mean diameter (D) of said droplets is comprised between about 30 nm and about 6000 nm. For some applications of the emulsions obtained by the process according to the present description, the mean diameter (D) of the droplets of the lipid phase is preferably within a predetermined range of values. For example, emulsions used in connection with oral bioavailability may involve lipid phases in the form of droplets with a mean diameter (D) preferentially less than 200 nm.

Furthermore, according to one or more embodiments of the present description the polydispersity index (PdI) of the emulsions may be preferentially less than 0.5, for example less than 0.3, or even less than 0.2. For certain emulsions obtained by the process according to one or more embodiments of the present description, a polydispersity index greater than 0.3 may reflect a poorer stability of the emulsion, which may, for example, be reflected by a poorer resistance to freeze-drying.

The process according to the present description further comprises adding at least one cryoprotectant to the mixture. This addition takes place after emulsifying the mixture. According to one or more embodiments, the concentration of cryoprotectant in the mixture excluding the source is comprised between 5 mg/mL (or 0.5% w/v, when expressed as a weight-to-volume ratio based on the total volume of the mixture) and 250 mg/mL (or 25% w/v). In particular, adding a cryoprotectant can provide additional protection to the emulsions obtained after emulsifying, for example during the freeze-drying step. The cryoprotectant can on the one hand replace the hydrogen bonds between water and surfactant, thus maintaining the spatial organization of the emulsion, and on the other hand can decrease the interactions between surfactants of different droplets, generating aggregates, and thus avoid the destabilization of the emulsion droplets. Moreover, the cryoprotectant can form an amorphous matrix and avoid the formation of ice crystals, as these can be the cause of droplet destabilization mechanisms.

According to one or more embodiments the at least one cryoprotectant is selected from the group comprising polymers, amino acids, saccharide compounds such as mono-, di- and polysaccharides, and combinations thereof. According to one or more embodiments, the at least one cryoprotectant is selected from the group comprising trehalose, sucrose, maltose, glucose, mannitol, hydroxypropyl-β-cyclodextrin, and combinations thereof. In other example embodiments, the at least one cryoprotectant is a polymer, such as a polyvinylpyrrolidone or a polyvinyl alcohol. The at least one cryoprotectant may also be an amino acid, such as glycine.

According to one or more embodiments, the concentration of the at least one cryoprotectant in the mixture excluding the source is comprised between 5 mg/mL (or 0.5% w/v) and 250 mg/mL (or 25% w/v), and selected based on factors such as system composition, cooling rate as well as freezing temperature. According to the first aspect of the present disclosure, the addition of the at least one cryoprotectant is made after the mixture has been emulsified, in a weight-to-volume ratio of at least 5% w/v based on the total volume of the mixture excluding the source, for example, comprised between 5% w/v and 10% w/v, for example, comprised between 6% w/v and 8% w/v. Adding a cryoprotectant in such concentrations can, for example, increase the homogeneity of emulsions obtained by an extraction process according to the present description comprising a step of freeze-drying the emulsion followed by a rehydration step.

According to one or more embodiments, the at least one lipophilic compound, the at least one surfactant and the at least one cryoprotectant are biocompatible. A biocompatible substance is defined as a substance without toxic or harmful effects on health and usable for cosmetic and/or pharmaceutical and/or food applications. For example, according to one or more embodiments, the at least one surfactant and the at least one cryoprotectant can be considered harmless according to the criteria recognized by the United States Food and Drug Administration (USFDA) and benefit from the generally recognized as safe (GRAS) designation.

According to one or more embodiments, the process further comprises a "post-extraction" treatment step, i.e., a step subsequent to emulsifying the mixture, thereby forming an emulsion. This treatment step can for example comprise a subsequent step of sonicating the emulsion obtained after emulsifying the mixture: this treatment step can then be performed, for example, by means of an ultrasonic rod (sonotrode).

The "post-extraction" treatment step may also, for example, comprise one or more ultra-centrifugation steps at speeds between 1000 G and 50 000 G. According to one or more embodiments, this treatment step may lower both the mean diameter D of the droplets and the polydispersity index of the emulsion.

According to one or more embodiments, the process further comprises a step of pretreating prior to emulsifying of the mixture, comprising hot maceration of the mixture comprising the water, the source, the at least one surfactant, and the at least one lipophilic compound, at a temperature comprised between about 20° C. and about 60° C. According to one or more embodiments, the step of pretreating may also comprise grinding, passing through a disperser-homogenizer (e.g., Ultraturrax®), an ultrasonic bath, or a microwave oven depending on the source to be extracted.

The process according to the present description further comprises freeze-drying the emulsion. For example, the freeze-drying step may be performed after emulsifying and adding at least one cryoprotectant. The emulsion freeze-drying step can lead to the formation of an emulsion in the form of a dry formulation. Thus, in a minimum of steps, dry formulations enriched in potentially bioactive and fat-soluble substances can be obtained. The corresponding emulsions are easy to reconstitute, by simple rehydration, i.e., by adding a certain amount of water or aqueous solution to the dry formulation to reform an emulsion. The reconstituted emulsion will not necessarily have the same characteristics as the starting emulsion, i.e., the emulsion before freeze-drying. For example, the mean droplet diameter D and/or the polydispersity index PdI of the reconstituted emulsion may differ substantially from their values in the emulsion before freeze-drying and after freeze-drying/rehydration (i.e., freeze-drying followed by rehydration). According to one or more embodiments, the process comprising freeze-drying the emulsion followed by a rehydration step, further comprises a "post-rehydration" treatment step, i.e., a step subsequent to the rehydration of a dry formulation obtained by freeze-drying. This step can for example consist of sonicating the emulsion obtained after rehydration, performed for example by means of an ultrasonic rod (sonotrode). According to one or more embodiments, this step may lower both the mean diameter D of the droplets and the polydispersity index of the emulsion obtained after rehydration.

The freeze-drying step can be adapted to the nature of the substance of interest and its inherent sensitivity, as well as to the volume of the mixture after emulsifying. The duration of the freeze-drying step may vary from a few hours to several days.

According to one or more embodiments, the freeze-drying step comprises at least three substeps: freezing where the mixture after emulsifying is brought to a temperature below about −20° C.; sublimation takes place at a pressure below about 500 µbar in order to sublimate the water of said mixture; and drying where said resulting mixture is brought to a temperature above about 20° C. in order to decrease the residual moisture content.

During the freeze-drying step, the at least one cryoprotectant can provide stability to the emulsion during the heat treatment it undergoes.

According to a second aspect, the present description relates to a dry formulation obtained by the process according to the first aspect.

In order to ensure the stability, preservation and storage of the emulsions produced by the process according to the first aspect, the present invention includes their transformation into dry formulations, by freeze-drying the emulsions, in order to facilitate and extend their field of use to various industrial sectors. Said dry formulations, obtained by freeze-drying the emulsions, make it possible, among other advantages, to limit any oxidation-type degradation of the substances of interest which they contain. Thus, the present description may relate to a dry formulation.

The present description makes it possible to obtain in a minimum of steps, by a "one-pot" process, dry formulations that are enriched in potentially bioactive liposoluble substances and easy to reconstitute by simple rehydration. In addition to their interest in terms of storage, preservation and use, these formulations could improve the stability and bioavailability of bioactive molecules, which opens up prospects for applications in various fields, some of which are high value-added, such as cosmetics, food processing or the pharmaceutical industry. In the case of extracts for food (e.g., food supplements or additives) or pharmaceutical purposes, such formulations can for example improve the oral bioavailability of the poorly water-soluble molecules they contain.

According to a further aspect, the present description relates to the use of the dry formulation according to the second aspect, in the manufacture of a product containing at least one substance of interest extracted from a source comprising the at least one substance of interest or at least one precursor thereof, by adding a compound selected from the group comprising water or an oil to said dry formulation.

According to another aspect, the present description relates to the use of the dry formulation according to the second aspect in the fields of cosmetics, food processing, pharmaceuticals, probiotics and/or nutraceuticals.

The embodiments described above are not exhaustive. In particular, it is understood that additional embodiments may be contemplated based on different combinations of the explicitly described embodiments. Unless otherwise specified in the present description, it will be apparent to the person skilled in the art that all of the above-described embodiments may be combined with each other. For example, unless otherwise specified, all features of the above-described embodiments, regardless of which embodiments of the process they refer to, may be combined with or replaced by other features of other embodiments.

Embodiments according to the above referenced aspects as well as additional advantages will become apparent from the following detailed description and the appended claims.

BRIEF DESCRIPTION OF THE FIGURES

FIG. 1, a schematic diagram illustrating an example of a process according to an embodiment of the invention.

DETAILED DESCRIPTION

In the following detailed description of embodiments of the present invention, a number of specific details are set forth to provide a more thorough understanding of the present description. However, it will be apparent to the skilled person that the present description can be implemented without these specific details. In other instances, well-known features have not been described in detail to avoid unnecessarily complicating the description.

FIG. 1 illustrates an embodiment of the extraction process according to the present description, further comprising an additional step of freeze-drying an emulsion obtained by sonication. The mixture to be emulsified comprises water (1), a plant source (2), i.e., *Curcuma longa* root, a surfactant (3), a lipophilic compound (4). The mixture is contained in a container (5), and emulsifying the mixture comprises a step of sonicating performed by means of an ultrasonic rod (6), capable of emitting ultrasonic waves (7). Sonicating the mixture leads to the formation of an emulsion comprising a continuous aqueous phase (10) and a discontinuous lipid phase in the form of droplets (40) having a certain content of substance of interest (21), i.e., in this case, curcumin. A cryoprotectant is then added to the mixture, and the freeze-drying step leads to the formation of a dry formulation (400). Adding water to this dry formulation, i.e., rehydration, can allow the dry formulation to rehydrate and leads to an emulsion with the same characteristics as before drying. However, in embodiments of the extraction process according to the present description other than that illustrated in FIG. 1, rehydration of the emulsion may lead to an emulsion having different characteristics than the emulsion before drying, e.g., in terms of mean diameter D and polydispersity index.

Example embodiments of an extraction process according to the present description are detailed below, in which the chosen source is a *Curcuma longa* root in order to extract curcumin, the substance of interest. Curcumin is a polyphenol whose varied pharmacological properties (anti-inflammatory, antioxidant, anticancer, treatment of certain neurodegenerative diseases, etc.) are only partially explored to date.

Moreover, curcumin shows a low solubility in water (11 ng/ml in a buffer solution pH=5), which makes the process according to the present description particularly attractive for extracting curcumin from *Curcuma longa*. Prior to their attempts to extract curcumin, the inventors tested the solubility of this molecule in various lipophilic compounds, by HPLC assay. Among the lipophilic compounds tested, tributyrin, in particular, proved to be a good candidate. Interestingly, this lipophilic compound is a biocompatible oil, which may make it attractive for certain applications of the process of the invention in the fields of cosmetics, food processing, pharmaceuticals, nutraceuticals and/or probiotics.

The emulsions numbered 12 to 18, for which certain characteristic conditions of the process for obtaining them, which are otherwise identical, have been collected in Table 1, are emulsions obtained by the process of the invention according to as many different example embodiments of the process of the invention. These embodiments of the process resulting in emulsions 12 to 18 all involve the use of the surfactant TPGS 1000 (α-tocopheryl polyethylene glycol 1000 succinate), namely a commercial surfactant derived from vitamin E (tocopherol), as well as the use of tributyrin as at least one lipophilic compound in the mixture. In emulsions 13 to 18, a second lipophilic compound was added to the mixture provided by the process, in the form of a wax, i.e., jasmine wax for emulsion 13 and Suppocire NB for emulsion 14, or in the form of another oil, i.e., C8-C10 triglycerides for emulsion 18.

As apparent for emulsion 14, the inventors succeeded in obtaining, via the process of the invention, an emulsion containing a curcumin content corresponding to an extraction rate of 100%. This extraction rate, fixed at 100% in acetone for a Soxhlet extraction set-up for 8 hours, was obtained under the inventors' conditions in only 2 minutes of sonicating the mixture leading to the formation of emulsion 14.

TABLE 1

| Emulsion | 12 | 13 | 14 | 18 |
|---|---|---|---|---|
| $m_{tributyrin}$ (mg) | 206 | 181 | 175 | 85 |
| $m_{C8-C10\ triglycerides}$ (mg) | 0 | 0 | 0 | 15 |
| $m_{SuppocireNB}$ (mg) | 0 | 0 | 25 | 0 |
| $m_{jasmine\ wax}$ (mg) | 0 | 25 | 0 | 0 |
| $m_{Curcuma\ longa}$ (mg) | 100 | 100 | 100 | 100 |
| $m_{TPGS\ 1000}$ (mg) | 60.8 | 60.8 | 60.8 | 60.8 |
| $m_{H2O}$ (mg) | 2027.6 | 2027.6 | 2027.6 | 2027.6 |
| D (nm) | 286.5 | 168.3 | 194.7 | 113 |
| PdI | 0.296 | 0.232 | 0.254 | 0.257 |
| Extraction rate (%) | 67 | 88 | 100 | 93 |

Moreover, it appears that replacing an amount of the first compound, i.e., tributyrin, with an amount approximately equal to its mass equivalent in jasmine wax (emulsion 13) or SuppocireNB (emulsion 14) improves the extraction rate and reduces the polydispersity index PdI, compared with emulsion 12 obtained only from tributyrin. Some protocol details for the production and analysis of emulsions 12 to 18 are provided in the paragraphs below.

Protocol for Preparing Emulsions 12 to 18:

The lipophilic compound alone (tributyrin) or the two lipophilic compounds (tributyrin/C8-C10 triglycerides or tributyrin/jasmine wax or tributyrin/Suppocire NB) was/are weighed, with a certain ratio in the case of the mixture of two lipophilic compounds. Furthermore, in the case of an oil/wax mixture, the oil/wax mixture was placed in a 40° C. bath until a homogeneous mixture was obtained.

The aqueous phase was prepared by dispersing a surfactant (TPGS 1000) in Milli-Q® water. The aqueous phase was then added to the at least one lipophilic compound and the whole was stirred for 20 seconds using a vortex. This solution was then poured into a 50 mL conical centrifuge tube in which a certain mass of *Curcuma longa* was previously weighed (100 mg).

A coarse emulsion was prepared by emulsifying the at least one lipophilic compound, the aqueous phase and the plant source first by vortexing for 10 seconds and then placing the centrifuge tube in the ultrasonic bath for 5 minutes at room temperature.

From this coarse emulsion, a finer emulsion was then prepared using an ultrasonic probe (BIOBLOCK SCIENTIFIC, Vibracell 7504). The ultrasonic probe (3=13 mm) was placed in the centrifuge tube for 16.75 minutes (in pulsed mode, corresponding to 2 minutes of sonicating in total) in an ice bath. The temperature of the mixture during sonicating the mixture was measured and was in the range of about [4° C.-20° C.]. The duty cycle applied was 11.94% and the sonication intensity was 60% (450 W).

After removing the ultrasound probe from the emulsion, the same probe was dipped into a tube containing 2 mL of Milli-Q® water. The rinse water was then added to the emulsion and the whole was centrifuged 1 minute at 1100 G.

The resulting emulsion can then be diluted and aliquoted in 2 mL batches. 300 µL of an aqueous cryoprotectant solution (concentration 500 mg/mL), for example trehalose or maltose, can then be added. These aliquots can then be placed in the freezer overnight and freeze-dried for one day.

Analysis Protocol for Emulsions 12 to 18:

The supernatant obtained after centrifugation was recovered and the droplet size distribution was analyzed by dynamic light scattering (DLS) using a Nano-S Nanosizer (Malvern Instrument). The supernatant, diluted 1:10 in Milli-Q® water, was placed in a 45 µL quartz cell and underwent 10 measurements of 10 seconds each. The hydrodynamic diameter or mean diameter D was obtained by averaging the results of the 10 measurements. The measurements were performed at an angle of 173° using a laser with a wavelength of 633 nm. The DLS data are calculated on an intensity basis.

The curcumin concentration of the supernatant was determined by high-performance liquid chromatography after diluting the emulsion in acetonitrile and then filtered through 0.2 µm nylon syringe filter.

A Shimadzu system with a diode array detector (SPD-M20A) was equipped with a pumping system (LC-20 AD), a degasser (DGU-20A3), a communication module (CBM-20A) and a column oven (Waters). Separation was performed on a Phenomenex Kinetex Biphenyl column (100 Å, 4.6*100 mm, 2.6 µm) with a column temperature set at 30° C. Data analysis was performed with the LabSolution software.

A linear gradient of A (water containing 0.1% trifluoroacetic acid) and B (acetonitrile containing 0.1% trifluoroacetic acid) was used with an elution gradient as follows (v/v): 0 min, B 37%; 10 min, B 50%; 15 min, B 100% maintained for 10 min. The flow rate was 1.3 mL/min and the injection volume was 5 Detection was obtained at 420 nm.

The following Tables 2 to 9 collect certain characteristics of emulsions, i.e., emulsions 19 to 65, prepared according to one or more embodiments of the process of the invention. These emulsions were prepared according to non-detailed embodiment protocols but similar to those described above for the preparation of emulsions 12 to 18. The analysis protocol for emulsions 19 to 65, on the other hand, is identical to that used for emulsions 12 to 18.

Each Table 2 to 9 aims to present comparable results as obtained under otherwise identical conditions.

TABLE 2

| Emulsion | 19 | 18 | 20 | 22 |
|---|---|---|---|---|
| $m_{tributyrin}$ (mg) | 100 | 85 | 85 | 42.5 |
| $m_{C8-C10\ triglycerides}$ (mg) | 0 | 15 | 0 | 0 |
| $m_{SuppocireNB}$ (mg) | 0 | 0 | 15 | 7.5 |
| $m_{Curcuma\ longa}$ (mg) | 100 | 100 | 100 | 100 |
| $m_{TPGS\ 1000}$ (mg) | 60.8 | 60.8 | 60.8 | 60.8 |
| $m_{H2O}$ (mg) | 2027.6 | 2027.6 | 2027.6 | 2027.6 |
| D (nm) | — | 113 | 109 | — |
| PdI | >0.3 | 0.257 | 0.251 | >0.3 |
| Extraction rate (%) | 74 | 93 | 87 | 82 |

Table 2 shows emulsions 19 and 20 prepared by weighing the same total mass of lipophilic compound(s) as emulsion 18 of Table 1, namely 100 mg. The results show in particular the benefit of adding a second lipophilic compound in order to reduce the PdI. Emulsion 22 corresponds to emulsion 20 for which the mass of lipophilic compound has been reduced by half, i.e., 50 mg, to the detriment of the homogeneity of the emulsion, whose PdI is higher than 0.3.

The inventors also showed that emulsion 18, when freeze-dried in the presence of 6.5% (w/v) trehalose (used as cryoprotectant) and then rehydrated, has a D of 147 nm and a PdI of 0.26 (result not shown in Table 2).

TABLE 3

| Emulsion | 23 | 24 | 25 | 26 | 27 |
|---|---|---|---|---|---|
| $m_{tributyrin}$ (mg) | 100 | 100 | 100 | 100 | 100 |
| $m_{Curcuma\ longa}$ (mg) | 100 | 150 | 200 | 250 | 300 |
| $m_{TPGS\ 1000}$ (mg) | 60.8 | 60.8 | 60.8 | 60.8 | 60.8 |
| $V_{H2O}$ (mL) | 4000 | 4000 | 4000 | 4000 | 4000 |
| D (nm) | — | 134 | 112 | 111 | 119 |
| PdI | >0.3 | 0.278 | 0.234 | 0.209 | 0.182 |
| Extraction rate (%) | 87 | 90 | 87 | 94 | 97 |

Table 3 indicates that the extraction rate increases with increasing amount of source (Curcuma longa) included in the mixture, as does the homogeneity of the emulsions, which for the latter results in a decrease in PdI.

TABLE 4

| Emulsion | 27 | 28 | 29 | 30 | 31 |
|---|---|---|---|---|---|
| $m_{tributyrin}$ (mg) | 100 | 100 | 100 | 100 | 100 |
| $m_{Curcuma\ longa}$ (mg) | 300 | 300 | 300 | 300 | 300 |
| $m_{TPGS\ 1000}$ (mg) | 60.8 | 60.8 | 60.8 | 60.8 | 60.8 |
| $V_{H2O}$ (mL) | 4000 | 4000 | 4000 | 4000 | 4000 |
| Post-extraction (centrifugation) | 1100 G 1 min | 1100 G 1 min + 5000 G 5 min | 1100 G 1 min + 10000 G 5 min | 1100 G 1 min + 15000 G 5 min | 1100 G 1 min + 20000 G 5 min |
| D (nm) | 119 | 116 | 116 | 115 | 113 |
| PdI | 0.182 | 0.127 | 0.116 | 0.112 | 0.114 |
| Extraction rate (%) | 97 | 81 | 77 | 83 | 81 |

Unlike the opaque emulsion 27, emulsions 28 to 31 presented in Table 4 are translucent, due to the inclusion in the extraction process from which they are derived of a "post-extraction" treatment step comprising several ultra-centrifugation steps.

The addition of a second ultra-centrifugation step in the post-treatment step results in a slight decrease in the extraction rate, but also in an increase in the homogeneity of the emulsions reflected by the decrease in PdI.

TABLE 7-continued

| | | | |
|---|---|---|---|
| $V_{H2O}$ (mL) | 6000 | 6000 | 6000 |
| D (nm) | 88 | 134 | 121 |
| PdI | 0.260 | 0.230 | 0.240 |
| Extraction rate (%) | 77 | 83 | 83 |

TABLE 5

| Emulsion | 32 | 33 | 34 | 35 | 36 |
|---|---|---|---|---|---|
| F1 | Tributyrin | Capryol90 | Squalene | Tocopherol | Triglycerides (C8-C10) |
| $m_{F1}$ (mg) | 100 | 100 | 100 | 100 | 100 |
| $m_{Curcuma\ longa}$ (mg) | 100 | 100 | 100 | 100 | 100 |
| $m_{TPGS\ 1000}$ (mg) | 60.8 | 60.8 | 60.8 | 60.8 | 60.8 |
| $m_{H2O}$ (mg) | 2027.6 | 2027.6 | 2027.6 | 2027.6 | 2027.6 |
| Pretreating | UltraTurrax ® | UltraTurrax ® | UltraTurrax ® | UltraTurrax ® | UltraTurrax ® |
| D (nm) | — | — | 138 | 199 | — |
| PdI | >0.3 | >0.3 | 0.230 | 0.277 | >0.3 |
| Extraction rate (%) | 76 | 80 | 79 | 83 | 81 |

Table 5 shows the influence of the nature of the lipophilic compound in the context of emulsions comprising a single lipophilic compound (or Fat 1, F1).

The series of emulsions 32 to 36 presented in Table 5 shows in particular the good homogeneity of emulsions containing tocopherol (also called vitamin E) or squalene as lipophilic compounds.

TABLE 6

| Emulsion | 35 | 37 | 38 | 39 |
|---|---|---|---|---|
| F1 | Tocopherol | Tocopherol | Tocopherol | Tocopherol |
| $m_{F1}$ (mg) | 100 | 100 | 85 | 85 |
| $m_{squalene}$ (mg) | 0 | 0 | 15 | 0 |
| $m_{tributyrin}$ (mg) | 0 | 0 | 0 | 15 |
| $m_{Curcuma\ longa}$ (mg) | 100 | 100 | 100 | 100 |
| $m_{TPGS\ 1000}$ (mg) | 60.8 | 60.8 | 60.8 | 60.8 |
| $m_{H2O}$ (mg) | 2027.6 | 2027.6 | 2027.6 | 2027.6 |
| Pretreating | UltraTurrax ® | — | — | UltraTurrax ® |
| D (nm) | 199 | — | 136 | 133 |
| PdI | 0.277 | >0.3 | 0.226 | 0.245 |
| Extraction rate (%) | 83 | 76 | 79 | 71 |

Table 6 shows the influence of a specific step of pretreating, as well as the influence of the addition of a second lipophilic compound in the context of emulsions comprising tocopherol as lipophilic compound (or Fat 1, F1).

The results show that the pre-treatment step including a passage of the mixture to the disperser-homogenizer (Ultra-Turrax® type) lowers the PdI of the emulsions. The same effect is observed when a second lipophilic compound is used, compared with the case of a single lipophilic compound.

TABLE 7

| Emulsion | 40 | 41 | 42 |
|---|---|---|---|
| Emulsifying | Ultrasound 2 min | UltraTurrax ® 16 min | UltraTurrax ® 2 min |
| $m_{tributyrin}$ (mg) | 255 | 255 | 255 |
| $m_{C8-C10\ triglycerides}$ (mg) | 45 | 45 | 45 |
| $m_{Curcuma\ longa}$ (mg) | 300 | 300 | 300 |
| $m_{TPGS\ 1000}$ (mg) | 180 | 180 | 180 |

Table 7 compares an emulsion obtained by a process comprising a step of emulsifying the mixture by sonicating (emulsion 40) with two emulsions obtained by a process comprising a step of emulsifying by passage to the disperser-homogenizer (of the UltraTurrax® type).

The total sonicating time of 2 min for emulsion 40, shown in Table 7, corresponds to the total time that ultrasound is applied to the mixture. Similarly, for emulsions 41 and 42, the time shown is the total time the disperser-homogenizer is applied to the mixture.

The extraction rate and homogeneity of emulsions 41 and 42 (obtained with the disperser-homogenizer) are similar and slightly higher than the corresponding values characterizing emulsion 40 (obtained by sonicating).

The inventors have also shown that when the emulsions undergo a "post-extraction" treatment step consisting of ultracentrifugation at 5000 G for 5 min, the values of (D; PdI) for emulsions 40 and 42 are, respectively, (81; 0.200) and (111; 0.222) (result not shown in Table 7).

Tables 8 and 9 below present the characteristics of other emulsions obtained by extraction processes according to the present description, applying to sources other than *Curcuma longa* root, such as lavender flower (Table 8) or orange peel (Table 9).

In both cases, the source is a plant source and contains an essential oil representing the substance of interest.

Two different surfactants were used to extract the lavender essential oil, namely TPGS 1000 for emulsions 43 to 52 and $H_{12}TAC_5$ for emulsions 53 to 55. Emulsions 43 to 47, which do not contain sunflower oil, also illustrate the possibility that the at least one lipophilic compound is exclusively contained in the source, as contemplated in the present description according to one or more embodiments of the process. Table 8 further illustrates the use of a cryoprotectant (trehalose) in different amounts in order to lower the polydispersity index of the emulsions after freeze-drying/rehydration.

Emulsions 56-60, which do not contain sunflower oil, illustrate the possibility that the at least one lipophilic compound is exclusively contained in the source, as contemplated by the present description according to one or more embodiments of the process. Table 9 further illustrates the use of a cryoprotectant (trehalose) in different amounts to lower the polydispersity index of the emulsions after freeze-drying/rehydration.

TABLE 8

| Emulsion | Analysis conditions | $m_{sunflower\ oil}$ (mg) | $m_{lavender}$ (g) | TPGS 1000 (g/L) | $H_{12}TAC_5$ (g/L) | $V_{H2O}$ (mL) | Trehalose (% w/v) | D (nm) | PdI |
|---|---|---|---|---|---|---|---|---|---|
| 43 | Before | 0 | 2 | 0.66 | 0 | 15 | 0 | 120 | 0.226 |
| 44 | After | 0 | 2 | 0.66 | 0 | 15 | 0 | 252 | 0.399 |
| 45 | After | 0 | 2 | 0.66 | 0 | 15 | 6.5 | 173 | 0.247 |
| 46 | After | 0 | 2 | 0.66 | 0 | 15 | 10 | 167 | 0.243 |
| 47 | After | 0 | 2 | 0.66 | 0 | 15 | 15 | 152 | 0.216 |
| 48 | Before | 10 | 1.25 | 1 | 0 | 10 | 0 | 106 | 0.206 |
| 49 | After | 10 | 1.25 | 1 | 0 | 10 | 0 | 338 | 0.551 |
| 50 | After | 10 | 1.25 | 1 | 0 | 10 | 6.5 | 172 | 0.177 |
| 51 | After | 10 | 1.25 | 1 | 0 | 10 | 10 | 177 | 0.163 |
| 52 | After | 10 | 1.25 | 1 | 0 | 10 | 15 | 152 | 0.173 |
| 53 | Before | 10 | 1.25 | 0 | 1 | 10 | 0 | 132 | 0.209 |
| 54 | After | 10 | 1.25 | 0 | 1 | 10 | 0 | 460 | 0.545 |
| 55 | After | 10 | 1.25 | 0 | 1 | 10 | 6.5 | 137 | 0.218 |

TABLE 9

| Emulsion | Analysis conditions | $m_{sunflower\ oil}$ (mg) | $m_{orange\ peel}$ (g) | TPGS 1000 (g/L) | $V_{H2O}$ (mL) | Trehalose (% w/v) | D (nm) | PdI |
|---|---|---|---|---|---|---|---|---|
| 56 | Before | 0 | 2 | 1 | 10 | 0 | 137 | 0.160 |
| 57 | After | 0 | 2 | 1 | 10 | 0 | 160 | 0.462 |
| 58 | After | 0 | 2 | 1 | 10 | 6.5 | 146 | 0.362 |
| 59 | After | 0 | 2 | 1 | 10 | 10 | 159 | 0.426 |
| 60 | After | 0 | 2 | 1 | 10 | 15 | 152 | 0.343 |
| 61 | Before | 10 | 2 | 1 | 10 | 0 | 137 | 0.201 |
| 62 | After | 10 | 2 | 1 | 10 | 0 | 140 | 0.914 |
| 63 | After | 10 | 2 | 1 | 10 | 6.5 | 126 | 0.970 |
| 64 | After | 10 | 2 | 1 | 10 | 10 | 233 | 0.734 |
| 65 | After | 10 | 2 | 1 | 10 | 15 | 131 | 0.967 |

The invention claimed is:

1. A process for extracting at least one substance of interest from a source, the process comprising the following steps of:

providing a mixture comprising water, at least one surfactant, at least one lipophilic compound, and a source, the source comprising the at least one substance of interest or at least one precursor thereof; and emulsifying the mixture, thereby forming an emulsion and extracting the at least one substance of interest from the source;

wherein the emulsion comprises:

a continuous aqueous phase; and a discontinuous lipid phase comprising the at least one lipophilic compound, the at least one surfactant, and the at least one substance of interest extracted from the source during emulsifying;

wherein the source is a plant source containing at least a portion of at least one plant, an animal source containing at least one part of at least one animal, a mineral source, a prokaryote source, and/or a unicellular eukaryote source; and wherein the process further comprises adding at least one cryoprotectant to the mixture and freeze-drying the emulsion; and wherein adding at least one cryoprotectant to the mixture is performed after emulsifying the mixture, in a weight-to-volume ratio of at least 5% w/v based on the total volume of the mixture excluding the source.

2. The process of claim 1, wherein emulsifying the mixture comprises sonicating the mixture.

3. The process of claim 1, wherein the source is a plant source containing at least a portion of at least one plant.

4. The process of claim 1, wherein the at least one surfactant is selected from the group consisting of Dendri-TAC type dendrimers, $F_iTAC_n$ or $F_iTAC_n$ type oligomers, TPGS 1000, TPGS 750M, sugar- and/or amino acid-derived surfactants, and combinations thereof.

5. The process of claim 1, wherein emulsifying is performed by maintaining the temperature of the mixture between about 4° C. and about 60° C.

6. The process of claim 1, wherein the duration of emulsifying is comprised between about 0.5 seconds and about 5 hours.

7. The process of claim 1, wherein said discontinuous lipid phase is in the form of droplets of a predetermined mean diameter.

8. The process of claim 1, wherein the at least one cryoprotectant is selected from the group consisting of polymers, amino acids, saccharide compounds, and combinations thereof.

9. The process of claim 1, wherein the at least one lipophilic compound, the at least one surfactant, and the at least one cryoprotectant are biocompatible.

10. The process of claim 1, further comprising a step of pretreating prior to emulsifying the mixture, wherein the step of pretreating comprises macerating the mixture at a temperature between about 20° C. and about 60° C.

* * * * *